(12) United States Patent
Sasaki et al.

(10) Patent No.: US 7,268,344 B2
(45) Date of Patent: Sep. 11, 2007

(54) SCANNING LASER MICROSCOPE APPARATUS

(75) Inventors: Kunihiko Sasaki, Hino (JP); Yasunari Matsukawa, Asaka (JP); Hiroshi Sasaki, Tokyo (JP); Tatsuo Nakata, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/447,761

(22) Filed: Jun. 6, 2006

(65) Prior Publication Data

US 2006/0278530 A1 Dec. 14, 2006

(30) Foreign Application Priority Data

Jun. 13, 2005 (JP) .............................. 2005-172144

(51) Int. Cl.
*G01J 1/32* (2006.01)

(52) U.S. Cl. ........................ 250/234; 250/205; 359/368

(58) Field of Classification Search ........ 250/234–236, 250/205, 201.3, 307, 310, 311; 359/368, 359/372, 385
See application file for complete search history.

(56) References Cited

U.S. PATENT DOCUMENTS 6,392,794 B1 * 5/2002 Engelhardt et al. ......... 359/368

FOREIGN PATENT DOCUMENTS

JP 11-174332 A 7/1999
JP 2004-219513 A 8/2004

* cited by examiner

*Primary Examiner*—Kevin Pyo
(74) *Attorney, Agent, or Firm*—Frishauf, Holtz, Goodman & Chick, P.C.

(57) ABSTRACT

A scanning laser microscope that can quantitatively display a laser irradiation power on a display unit and that can suppress fluctuations in the laser irradiation power is provided. The scanning laser microscope includes a light source configured to emit laser light, a scanning unit configured to scan the laser light emitted from the light source on a sample, a photodetector configured to detect light from the sample, a processing unit configured to convert a signal from the photodetector into an image signal of the sample and to output the image signal, a reference light detector configured to detect part of the laser light emitted from the light source as a reference light signal, a laser light control unit configured to control the power of the laser light emitted from the light source, an irradiation-power calculation unit configured to calculate an irradiation power value at the sample on the basis of the reference light signal detected by the reference light detector, and a display unit configured to display the calculated irradiation power value at the sample.

20 Claims, 8 Drawing Sheets

SCANNING LASER MICROSCOPE APPARATUS

BACKGROUND OF THE INVENTION

1. Field of the Invention

The present invention relates to a scanning laser microscope for observing a sample image illuminated with laser light. In particular, the present invention relates to a scanning laser microscope that can accurately monitor the power of laser light from a light source.

This application is based on Japanese Patent Application No. 2005-172144, the content of which is incorporated herein by reference.

2. Description of Related Art

A known laser microscope includes a light source that emits laser light having multiple wavelengths that are different from each other, an illumination optical system that irradiates a sample with the multi-wavelength laser light from the light source through an objective lens, an observation optical system that receives light emitted from the sample by irradiation of the multi-wavelength laser light to obtain a sample image, a beamsplitting unit that splits off part of the multi-wavelength laser light as reference light before the sample is irradiated with that light, a wavelength-selecting unit that selects a light component having a predetermined wavelength from the reference light split off by the beamsplitting unit, and an intensity-detecting unit that detects the intensity of the light component having the predetermined wavelength selected by the wavelength-selecting unit (for example, see Japanese Unexamined Patent Application Publication No. 11-174332).

Another known laser microscope includes a light source that emits laser light, a scanning unit that scans the laser light onto a sample, a photodetector that detects light from the sample, a processing unit that converts a signal from the photodetector into an image signal of the sample and that outputs the image signal, a reference light detector that detects part of the laser light emitted from the light source as reference light, a correction data processing unit that converts a signal from the reference light detector into correction data corresponding to the position on the sample illuminated with the laser light and that outputs the correction data, and a correcting device that corrects the image signal of the sample output from the processing unit on the basis of the correction data output from the correction data processing unit (for example, see Japanese Unexamined Patent Application Publication No. 2004-219513).

In the laser microscope disclosed in Japanese Unexamined Patent Application Publication No. 11-174332, the wavelength selection is performed using a turret plate including a plurality of bandpass filters provided on the side of the reference light or using an acousto-optical tunable filter (AOTF), and the light intensity is monitored.

The laser microscope disclosed in Japanese Unexamined Patent Application Publication No. 2004-219513 is designed so that even when the intensity of the laser light varies in detecting the reference light, the resulting image is not affected by the variation.

BRIEF SUMMARY OF THE INVENTION

The present invention provides a laser microscope that can quantitatively display a laser irradiation power on a display unit and that can suppress fluctuations in the laser irradiation power.

In order to achieve the object described above, the present invention provides the following solutions.

According to a first embodiment of the present invention, a scanning laser microscope includes a light source configured to emit laser light, a scanning unit configured to scan the laser light emitted from the light source on a sample, a photodetector configured to detect light from the sample, a processing unit configured to convert a signal from the photodetector into an image signal of the sample and to output the image signal, a reference light detector configured to detect part of the laser light emitted from the light source as a reference light signal, a laser light control unit configured to control the power of the laser light emitted from the light source, an irradiation-power calculation unit configured to calculate an irradiation power value at the sample on the basis of the reference light signal detected by the reference light detector, and a display unit configured to display the calculated irradiation power value at the sample.

In the first embodiment of the present invention, the irradiation-power calculation unit preferably converts the reference light signal into the irradiation power value at the sample on the basis of transmittance characteristic data of an optical system disposed between the sample and the reference light detector.

In the first embodiment of the present invention, the irradiation-power calculation unit preferably converts the reference light signal into the irradiation power value at the sample on the basis of transmittance characteristic data of an optical system disposed between the sample and the reference light detector, and the laser light control unit preferably corrects the power of the laser light emitted from the light source on the basis of the irradiation power value.

In the first embodiment of the present invention, the irradiation-power calculation unit preferably converts the reference light signal into the irradiation power value at the sample on the basis of at least one of spectral sensitivity characteristic data of the reference light detector and spectral transmittance characteristic data of an optical system disposed between the sample and the reference light detector.

Furthermore, in the first embodiment of the present invention, the irradiation-power calculation unit preferably converts the reference light signal into an irradiation power value per unit area on the sample and the display unit preferably displays the irradiation power value per unit area (this structure is referred to as first structure).

In this case, the unit area may correspond to the size of a single pixel in a scan image of the sample.

In the first embodiment of the present invention, the scanning laser microscope may further include an irradiation-light-intensity detector disposed at the position of the sample, and a data storage unit configured to associate a power command value of the laser light control unit or the reference light signal from the reference light detector with a measured irradiation power value at the sample measured by the irradiation-light-intensity detector and to store the data. In this scanning laser microscope, the irradiation-power calculation unit may determine an irradiation power by reading from the data storage unit the measured irradiation power value at the sample that is associated with the power command value or the reference light signal.

In this case, the scanning laser microscope may further include a power-command specifying unit. In this scanning laser microscope, the irradiation-power calculation unit preferably converts the irradiation power value at the sample into an irradiation power value per unit area on the sample, the power-command specifying unit preferably specifies a power command value that can achieve a desired irradiation power value for a specific area on the sample on the basis of the irradiation power value per unit area, and the laser light control unit preferably controls the light source on the basis of the power command value specified by the power-command specifying unit.

The data storage unit may store the information on the irradiation power value per unit area converted from the irradiation power value at the sample.

In the first structure of the present invention, the irradiation-power calculation unit may convert the reference light signal into the irradiation power value per unit area on the sample on the basis of a Gaussian density distribution.

In the first structure of the present invention, the display unit may display the irradiation power value per unit area, while updating the display after each pixel is scanned.

In the first structure of the present invention, the irradiation-power calculation unit may calculate a time-integrated value of the irradiation power per unit area on the basis of the irradiation power value per unit area, and the display unit may display the time-integrated value of the irradiation power (this structure is referred to as second structure).

In the first embodiment of the present invention, the display unit may display the irradiation power value at the sample, while updating the display after each pixel is scanned.

In the second structure of the present invention, the irradiation-power calculation unit may integrate the irradiation power per unit area while laser scanning is performed once.

Furthermore, in the first embodiment of the present invention, the irradiation-power calculation unit may calculate a time-integrated value of the irradiation power on the sample and the display unit may display the time-integrated value.

In this case, the irradiation-power calculation unit preferably integrates the irradiation power value at the sample while laser scanning is performed once.

According to a second embodiment of the present invention, a scanning laser microscope includes a light source configured to emit laser light, a scanning unit configured to scan the laser light emitted from the light source on a sample, a photodetector configured to detect light from the sample, a processing unit configured to convert a signal from the photodetector into an image signal of the sample and to output the image signal, a reference light detector configured to detect part of the laser light emitted from the light source as a reference light signal, a control device configured to control the power of the laser light emitted from the light source, an irradiation-power calculation device configured to calculate an irradiation power value at the sample on the basis of the reference light signal detected by the reference light detector, and a display unit configured to display the calculated irradiation power value at the sample.

In the second embodiment of the present invention, the irradiation-power calculation device may calculate an irradiation power value per unit area on the sample on the basis of the reference light signal, and the display unit may display the irradiation power value per unit area.

In the second embodiment of the present invention, the scanning laser microscope may further include a data storage device configured to associate a measured irradiation power value at the sample with a power command value from the control device to the light source or the reference light signal and to store the data. In this scanning laser microscope, the irradiation-power calculation device may determine an irradiation power value by reading from the data storage device the measured irradiation power value that is associated with the power command value or the reference light signal.

According to a third embodiment of the present invention, a scanning laser microscope includes a light source configured to emit laser light, a scanning unit configured to scan the laser light emitted from the light source on a sample, a photodetector configured to detect light from the sample, a processing unit configured to convert a signal from the photodetector into an image signal of the sample, a reference light detector configured to detect part of the laser light emitted from the light source as a reference light signal, a laser light control unit configured to control the power of the laser light emitted from the light source, an irradiation-power calculation unit configured to calculate an irradiation power value per unit area on the sample on the basis of the reference light signal detected by the reference light detector, and a display unit configured to display the calculated irradiation power value per unit area on the sample.

DETAILED DESCRIPTION OF THE INVENTION

A scanning laser microscope according to a first embodiment of the present invention will now be described with reference to the drawings.

Figure 1:
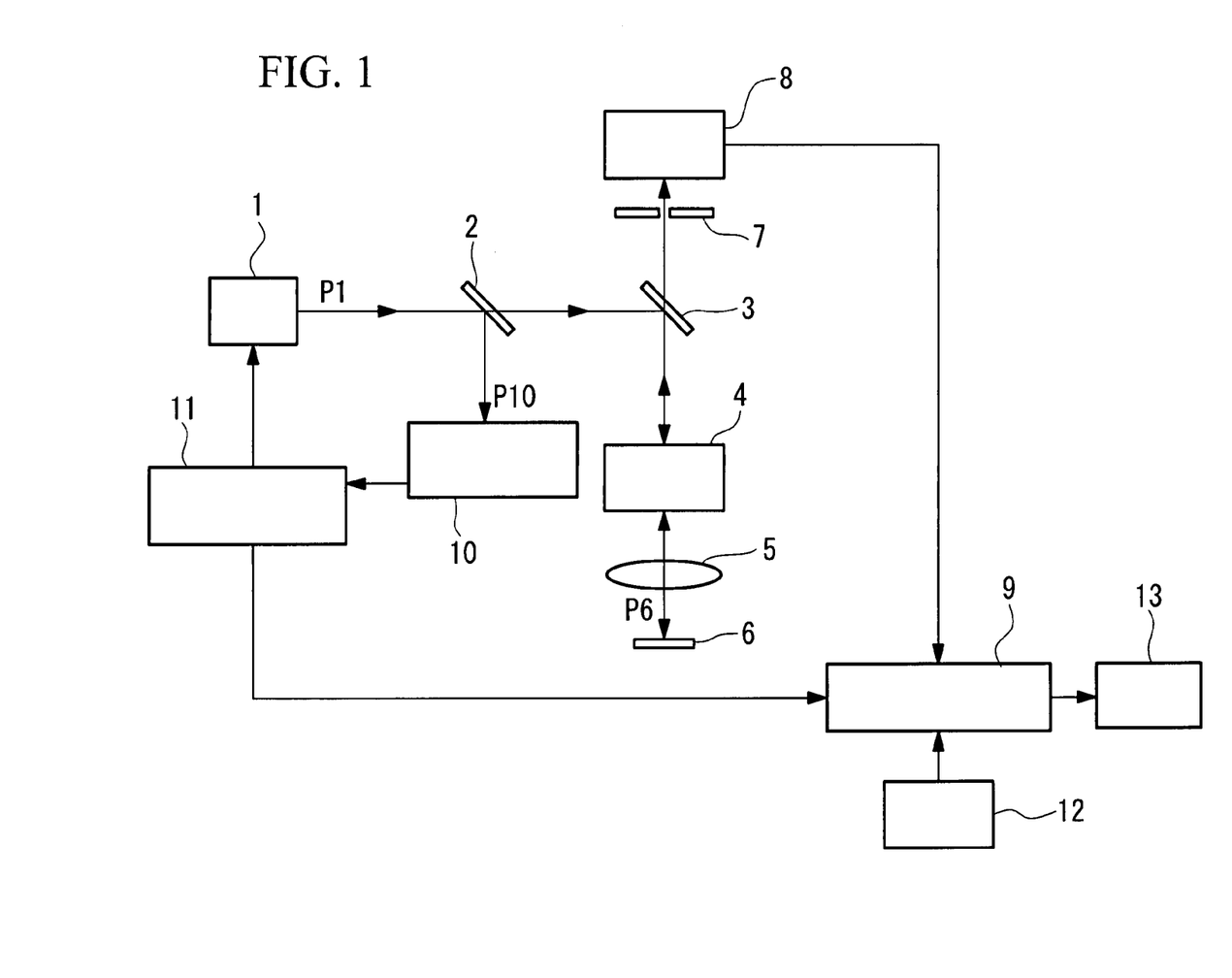
FIG. 1 is an overall structural diagram that schematically shows a scanning laser microscope according to a first embodiment and a second embodiment of the present invention.

FIG. 1 shows the general structure of a scanning laser microscope according to this embodiment.

The scanning laser microscope of this embodiment includes a light source 1 that emits laser light, a reference-light beamsplitting mirror 2 that splits off the laser light emitted from the light source 1 into irradiation light and reference light, a dichroic mirror 3 that reflects the irradiation light to direct it to a sample 6, a scanning unit 4 that scans the irradiation light in two directions, i.e., the X direction and the Y direction, which are orthogonal to the optical axis of the irradiation light, an objective lens 5 that radiates the scanned irradiation light onto the sample 6 and that collects fluorescence emitted from the sample 6, a pinhole member 7 that stops down the fluorescence collected by the objective lens 5 and passing through the scanning unit 4 and the dichroic mirror 3, and a photodetector 8 that detects the fluorescence passing through the pinhole member 7.

A system control unit 9 (processing unit) is connected to the photodetector 8. The system control unit 9 processes the fluorescence emitted from the sample 6 and detected by the photodetector 8 to display an examination image on a display unit 13.

The scanning laser microscope of this embodiment further includes a reference light detector 10 that detects the reference light split off by the reference-light beamsplitting mirror 2, and a laser light controller 11. The laser light controller 11 converts a reference light signal detected by the reference light detector 10 into an irradiation power value at the sample 6, and corrects a power command value sent to the light source 1 and displays the irradiation power value on the display unit 13 via the system control unit 9. That is, the laser light controller 11 in this embodiment functions as both a control device that controls the operation of the light source 1 to control the power of the laser light emitted from the light source 1 (i.e., a power-command specifying unit described below, which specifies the power command value) and an irradiation-power calculation unit that calculates the irradiation power value (the function of this irradiation-power calculation unit may be provided in the system control unit 9).

On the basis of the setting of the wavelength and the power command value in the laser light controller 11, the light source 1 emits laser light having the predetermined wavelength with a power corresponding to the power command value.

The reference-light beamsplitting mirror 2 has a transmittance of $f2(\lambda)$ and a reflectance of $1-f2(\lambda)$.

The dichroic mirror 3 has a transmittance of $f3(\lambda)$ and a reflectance of $1-f3(\lambda)$ The scanning unit 4 changes the angle of inclination of a mirror so as to scan the irradiation light irradiated onto the sample 6 in the two directions, i.e., the X direction and the Y direction. The mirror of the scanning unit 4 has a transmittance of $f4(\lambda)=0$ and a reflectance of $1-f4(\lambda)=1$.

The objective lens 5 is disposed on the optical path. A magnification ratio suitable for observing the sample 6 in detail is selected for the objective lens 5 from among various available magnification ratios. The objective lens 5 has a transmittance of $f5(\lambda)$ and a reflectance of $1-f5(\lambda)$. $f2(\lambda)$, $f3(\lambda)$, and $f5(\lambda)$ are treated as spectral transmittance functions, that is, functions of the wavelength $\lambda$ of the laser light. However, when the wavelength characteristics of these optical elements are negligible, $f2(\lambda)$, $f3(\lambda)$, and $f5(\lambda)$ may be treated as constants.

The sample 6 is disposed at an appropriate position on the optical axis. When the sample 6 is irradiated with laser light having a predetermined wavelength, fluorescence having a wavelength different from that of the laser light is emitted with a luminance corresponding to the power of the laser light.

The pinhole member 7 is composed of, for example, a plate including a plurality of pinholes having diameters different from each other and provided at appropriate positions. Any one of the pinholes can be disposed on the optical axis of detection light by electrically revolving the plate, thus achieving a desired confocal effect.

The photodetector 8 includes a photomultiplier tube (PMT) that converts the power of the fluorescence passed through the pinhole member 7 into current, a current-voltage converting circuit, an A/D converting circuit, and the like so as to detect the power of the fluorescence.

The reference light detector 10 includes a photodiode and the like so as to detect the reference light reflected on the reference-light beamsplitting mirror 2.

An operating unit 12 is connected to the system control unit 9. The operating unit 12 is used for setting, for example, the scanning zone and the scanning speed of the scanning unit 4, setting the wavelength and the power command value of the laser light irradiating the sample 6, and controlling, for example, the initiation and the completion of the fluorescence observation. The display unit 13 displays the fluorescence image of the sample 6, the converted irradiation power value of the laser light on the sample 6 sent from the laser light controller 11, and the like.

The operation of the scanning laser microscope of this embodiment, having the above structure, will now be described.

In order to observe a sample using the scanning laser microscope of this embodiment, first, an initial fluorescence-observation operation is performed by setting the scanning zone and the scanning speed of the scanning unit 4, the wavelength and the power command value of laser light emitted from the light source 1, and the like using the operating unit 12. The laser light controller 11 outputs a signal for setting the power command value to the light source 1 on the basis of the set wavelength and the power command value of the laser light. The light source 1 outputs laser light P1 with a power corresponding to the set wavelength and the power command value. The output laser light P1 is incident on the reference-light beamsplitting mirror 2. Part of the laser light P1 is reflected with a reflectance of $1-f2(\lambda)$ and is incident on the reference light detector 10, and the rest, which is transmitted with a transmittance of $f2(\lambda)$, is incident on the dichroic mirror 3.

The laser light incident on the dichroic mirror 3 is reflected with a reflectance of $1-f3(\lambda)$ and is radiated onto the sample 6 through the scanning unit 4, having a reflectance of 1, and the objective lens 5, having a transmittance of $f5(\lambda)$. When the sample 6 is irradiated with the laser light, the sample 6 emits fluorescence having a wavelength different from the irradiated wavelength. The fluorescence is incident on the dichroic mirror 3 through the objective lens 5 and the scanning unit 4 and passes through the dichroic mirror 3 with a transmittance of $f3(\lambda)$. The transmitted fluorescence passes through the pinhole member 7 and is detected by the photodetector 8. A detection signal corresponding to the power of the fluorescence is transmitted to the system control unit 9.

The reference light reflected at the reference-light beamsplitting mirror 2 is introduced to the reference light detector 10, and the reference light detector 10 detects the power of the reference light. A detection signal is transmitted to the laser light controller 11 as a detected intensity P10. The laser light controller 11 converts the detected intensity P10 into a power value P6 of the laser light irradiated onto the sample 6 using the known reflectance 1−f2(λ) and the transmittance f2(λ) of the reference-light beamsplitting mirror 2, the reflectance 1−f3(λ) of the dichroic mirror 3, the reflectance 1 of the scanning unit 4, and the transmittance f5(λ) of the objective lens 5 using the following equation:

$$P6 = f5(\lambda) \times (1-f3(\lambda)) \times f2(\lambda)/(1-f2(\lambda)) \times P10$$

wherein λ is the wavelength of the laser used.

The converted irradiation power value P6 at the sample 6 is displayed on the display unit 13 through the system control unit 9. The laser light controller 11 compares this irradiation power value P6 with the power command value of the laser light set by the operating unit 12 before initiating the fluorescence observation. If the irradiation power value P6 is larger than the power command value, the laser light controller 11 decreases the power command value that is output to the light source 1. If the irradiation power value P6 is smaller than the power command value, the laser light controller 11 increases the power command value that is output to the light source 1. Thus, the irradiation power value P6 can be controlled so as not to deviate from the power command value. Regarding the display of the converted power value on the display unit 13, the unit can be switched to either milliwatt units or watt units, and the number of digits of the numerical value can be changed using the operating unit 12.

The signal corresponding to the power of the fluorescence transmitted to the system control unit 9 is used to form an array according to the position scanned by the scanning unit 4 to form a fluorescence image while the sample 6 is irradiated with the laser light with a stable power value and while the power value is displayed as described above. The resulting fluorescence image is displayed on the display unit 13 through the system control unit 9.

In the description of this embodiment, the sum of the transmittance and the reflectance is equal to 1. However, the present invention is not limited thereto. In the description of this embodiment, values such as the transmittance and the reflectance are treated as known values. Alternatively, the following method may be used: As a preliminary experiment prior to the observation, reference light is collected while laser light is radiated. Instead of the above calculation of the conversion equation, a lookup table showing the corresponding relationship between the power command value or the reference light signal and the measured irradiation power value is stored in a memory (data-storage unit). The conversion into the power of the laser light irradiated onto the sample 6 may be performed with reference to this lookup table. In this case, the characteristics of the intermediate optical system are reflected in the values in the memory as a collection result obtained in the preliminary experiment. Furthermore, a plurality of pinhole members 7, photodetectors 8, and dichroic mirrors (not shown) that separate the fluorescence for each wavelength may be provided one for each wavelength of the fluorescence to be detected. Furthermore, in order to improve the accuracy of the calculated numerical values, the spectral sensitivity characteristics f10(λ) of the reference light detector 10 may be considered. In this case, in the above equation, the output value P10 of the reference light detector 10 is replaced with f10(λ)×P10.

As described above, in the scanning laser microscope of this embodiment, part of the power of the laser light irradiated onto the sample 6 is detected using the reference light detector 10, and this part of the power is converted into a power value irradiated onto the sample 6. Thereby, the converted power value can be displayed and the power of the laser light emitted from the light source 1 can be corrected. In this scanning laser microscope, therefore, an operator can instantaneously recognize the irradiation power and the irradiation power can be kept stable so as to have a small fluctuation. Furthermore, this scanning laser microscope uses the values of transmittance and reflectance in each part by considering the wavelength λ. Thus, the converted power on the sample 6 can be obtained on the basis of at least one of the spectral sensitivity characteristic data of the reference light detector 10 and the spectral transmittance characteristic data of the optical system disposed between the sample 6 and the reference light detector 10. Consequently, it is possible to obtain converted power with high accuracy.

In this embodiment, the laser light controller 11 may convert the power value P6 into an irradiation power value per unit area, and may perform various processes on the basis of this irradiation power value per unit area.

A scanning laser microscope according to a second embodiment of the present invention will now be described.

In the description of this embodiment, parts common to those of the scanning laser microscope of the first embodiment are assigned the same reference numerals, and the description of those parts is omitted.

The scanning laser microscope of this embodiment differs from the scanning laser microscope of the first embodiment in the process performed in the system control unit 9. The system control unit 9 operates so that the reference light detected in the reference light detector 10 is converted into not only the irradiation power at the sample 6 but also a power density (i.e., an irradiation power per pixel or per predetermined unit area; a single pixel may be defined as the unit area) and the power density is displayed on the display unit 13. That is, the system control unit 9 in this embodiment functions as the irradiation-power calculation unit.

Figure 2A:
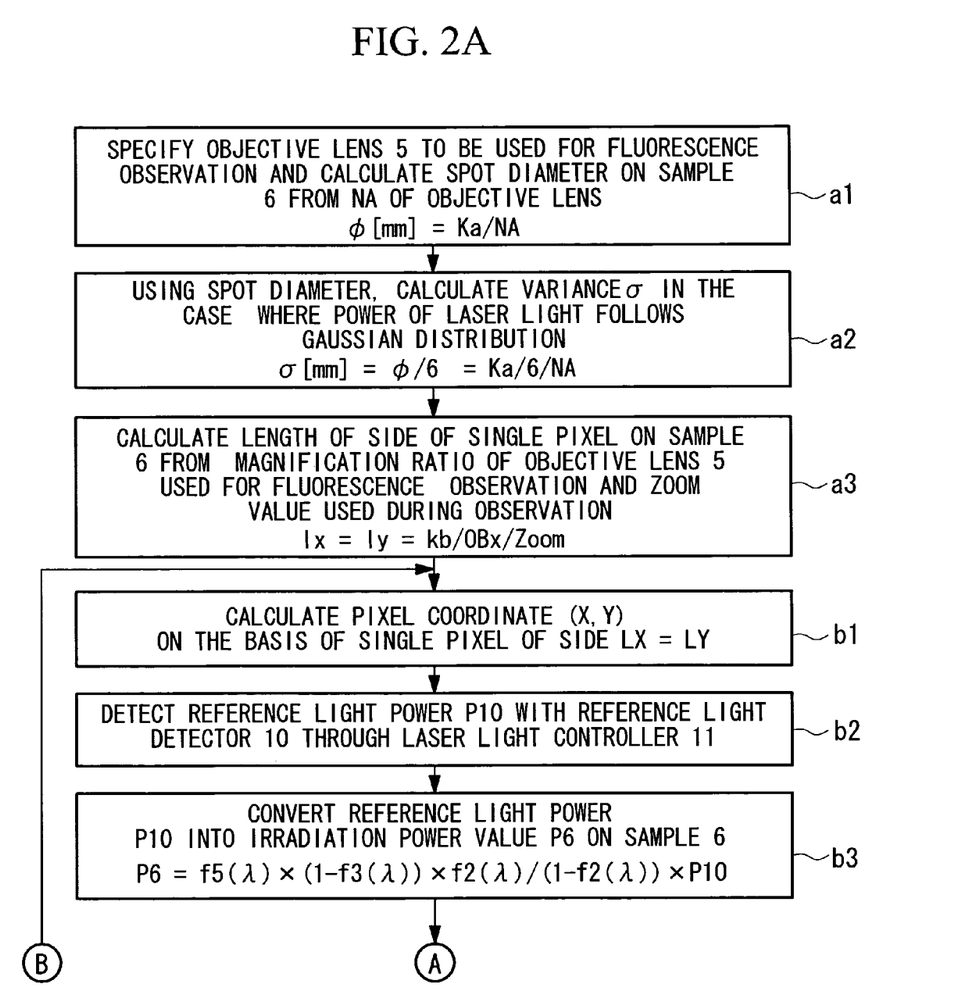
FIG. 2A is a flow chart showing an operation for displaying a power density in a system control unit of the scanning laser microscope shown in FIG. 1.
Figure 2B:
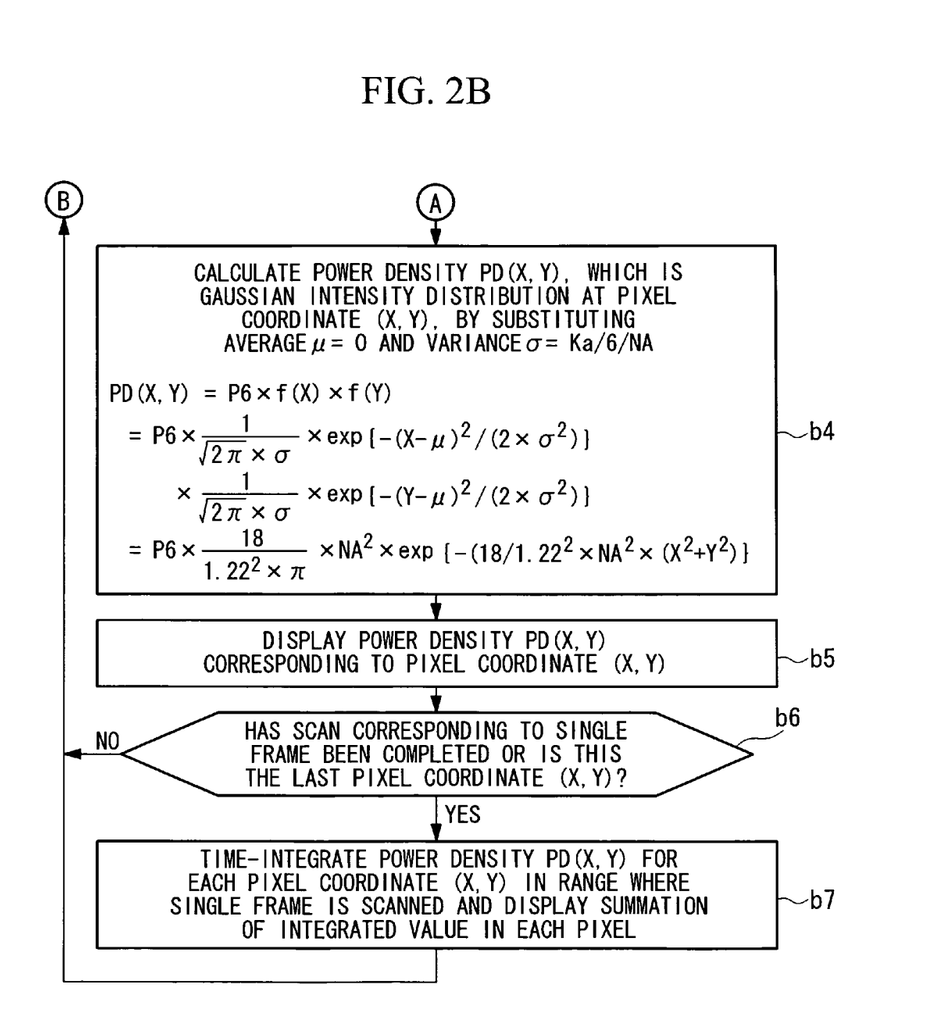
FIG. 2B is a flow chart showing an operation for displaying a power density in a system control unit of the scanning laser microscope shown in FIG. 1.

FIGS. 2A and 2B are a flow chart showing an operation for displaying the power density in the system control unit 9 according to the second embodiment of the present invention.

In the operation in step a1, an objective lens 5 to be used for fluorescence observation is specified, and a laser spot diameter on the sample 6 is calculated from the numerical aperture (NA) of the objective lens 5 by the following equation:

$$\phi[\text{mm}] = Ka/NA$$

wherein φ represents the laser spot diameter and Ka represents a constant.

In the operation in step a2, using the laser spot diameter, the variance σ in the case where the power of the laser light follows a Gaussian distribution is calculated by the following equation:

$$\sigma[\text{mm}] = \phi/6 = Ka/6/NA$$

In the operation in step a3, the length of a side (lx, ly) of a single pixel on the sample 6 is calculated from the magnification ratio of the objective lens 5 used for fluorescence observation and a zoom value used during observation by the following equation:

$$lx[mm]=ly[mm]=Kb/OBx/Zoom$$

wherein Kb represents a constant, OBx represents the magnification ratio of the objective lens, and Zoom represents a zoom magnification ratio. The zoom magnification ratio represents a magnification ratio in the case where the size of the observation field of view is adjusted by changing the angle of view of the scan (i.e., the magnitude of the rocking angle of the scanning mirror in the scanning unit 4).

In the operation in step b1, a pixel coordinate (X, Y) is calculated on the basis of the side lx=ly of a single pixel.

In the operation in step b2, the reference light power P 10 is detected by the reference light detector 10 through the laser light controller 11.

In the operation in step b3, by the same conversion method as that used in the first embodiment, the reference light power P10 is converted into the irradiation power value P6 at the sample 6 by the following equation:

$$P6=f5(\lambda)\times(1-f3(\lambda))\times f2(\lambda)/(1-f2(\lambda))\times P10$$

In the operation in step b4, the power density PD(X, Y), i.e., the Gaussian intensity distribution at a pixel coordinate (X, Y), is calculated by substituting an average of μ=0 and a variance of σ=Ka/6/NA for the following equation:

$$PD(X, Y) = P6 \times f(X) \times f(Y)$$
$$= P6 \times 1/(\sqrt{2\pi} \times \sigma) \times \exp\{-(X-\mu)^2/(2\times\sigma^2)\} \times$$
$$1/(\sqrt{2\pi} \times \sigma) \times \exp\{-(Y-\mu)^2/(2\times\sigma^2)\}$$
$$= P6 \times 18/1.22^2/\pi \times NA^2 \times$$
$$\exp\{-18/1.22^2 \times NA^2 \times (X^2 \times Y^2)\}$$

wherein f(X) represents a Gaussian intensity distribution at a pixel coordinate X, and f(Y) represents a Gaussian intensity distribution at a pixel coordinate Y.

In the operation in step b5, the power density PD(X, Y) corresponding to the pixel coordinate (X, Y) is displayed. In the operation in step b6, it is confirmed whether or not a scan corresponding to a single frame is completed. In the operation in step b7, the power density PD(X, Y) for each pixel coordinate (X, Y) is time-integrated in the range where the single frame is scanned, and the summation of the integrated value in each pixel is displayed. The value on the display is updated in each frame renewal.

The operations in steps a1 to a3 are performed in a set-up procedure before the fluorescence observation is started. The operations in steps b1 to b6 are repeated each time a pixel coordinate (X, Y) is shifted by a single pixel during scanning after the fluorescence observation is started. The operation in step b7 is repeated each time the scan corresponding to a single frame is completed.

In the scanning laser microscope of the second embodiment having the above structure, first, before the fluorescence observation is started, as described in steps a1 to a3, the system control unit 9 collects data on the NA of the objective lens 5 used, the magnification ratio OBx of the objective lens 5, and the zoom value Zoom during observation. The spot diameter φ [mm] of the laser light on the sample 6 and the variance σ [mm] in the case where the power of the laser light follows a Gaussian density distribution are calculated from the NA. The length of a side lx [mm]=ly [mm] of a single pixel on the sample 6 is calculated from the magnification ratio OBx and the zoom value Zoom. The information on these values is stored in a memory (not shown in the figure) in the system control unit 9.

When an initiation operation for fluorescence observation is performed by the operating unit 12, laser light is emitted from the light source 1, and the laser light is scanned on the sample 6 by the scanning unit 4. In this step, the laser light having a power following a Gaussian density function is radiated onto a pixel position (X, Y), which is the center of the laser scanning, on the sample 6. In step b2, the system control unit 9, which has determined the pixel position (X, Y) in step b1, detects the reference light power P10 by the reference light detector 10 through the laser light controller 11. In step b3, the system control unit 9 converts the reference light power P10 into the irradiation power value P6 at the sample 6 by the same conversion method as that used in the first embodiment.

Furthermore, in step b4, the system control unit 9 reads the values stored in the memory (not shown) and calculates the Gaussian intensity distribution at a pixel coordinate (X, Y), i.e., the power density PD(X, Y) by substituting the average μ and the variance σ. In step b5, the system control unit 9 displays the power density PD(X, Y) corresponding to the pixel coordinate (X, Y) on the display unit 13.

Furthermore, as shown in step b6, the system control unit 9 confirms whether a scan corresponding to a single frame is completed or not. In the case where the scan is completed, as shown in step b7, the power density PD(X, Y) for each pixel coordinate (X, Y) is time-integrated in the region where the single frame is scanned, and the summation of the power density PD(X, Y) of each pixel is displayed on the display unit 13.

The laser light is scanned by the scanning unit 4 to shift the pixel coordinate (X, Y) to the next pixel. The operations in steps b1 to b7 are repeated. When the pixel coordinate (X, Y) reaches the end position of the predetermined frame size, the coordinate (X, Y) returns to the initial scanning position, and the same operations are repeated or the fluorescence observation is completed.

As described above, according to the scanning laser microscope of this embodiment, even when the objective lens 5 is switched or the zoom is changed during observation, the irradiation power value of the laser light irradiated onto the sample 6 can be displayed on the basis of pixel units. In addition, the power value can be displayed as a power density not only per pixel unit but also based on various other unit areas.

Furthermore, the displayed power density in each pixel is updated according to the scanning position. Therefore, the change in the pixel position caused by the Gaussian density distribution depending on the scanning position can be checked with time. In addition, because a plurality of adjacent pixels can be selected or specified, the power densities of the pixels added, and the summation displayed, the irradiation power of a target area during observation can also be checked. Furthermore, since the summation of the time-integrated power density of each pixel is displayed, the converted irradiation power value of the laser light that is radiated while one frame is scanned can be checked while its value is updated in each frame.

Figure 3A:
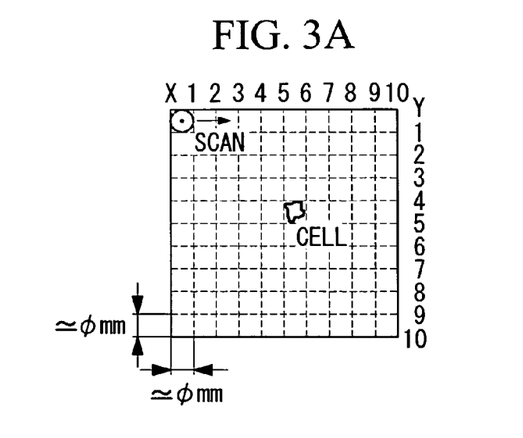
FIG. 3A is a view showing an example of an image of a cell examined and a spot of laser light irradiated, in the scanning laser microscope shown in FIG. 1.
Figure 3B:
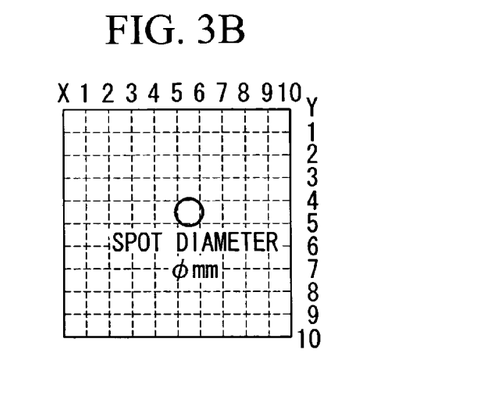
FIG. 3B is a view showing an example of an image of the cell examined and the spot of laser light irradiated, in the scanning laser microscope shown in FIG. 1.
Figure 3C:
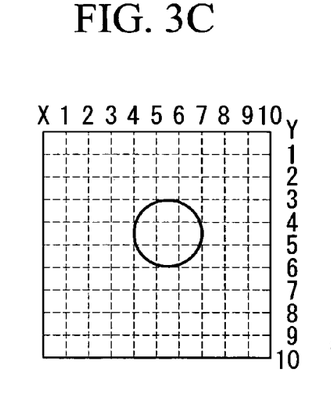
FIG. 3C is a view showing an example of an image of the cell examined and the spot of laser light irradiated, in the scanning laser microscope shown in FIG. 1.
Figure 3D:
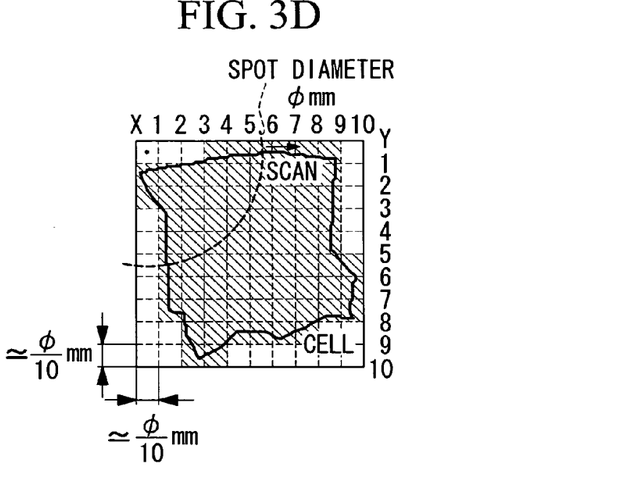
FIG. 3D is a view showing an example of an image of the cell examined and the spot of laser light irradiated, in the scanning laser microscope shown in FIG. 1.
Figure 3E:
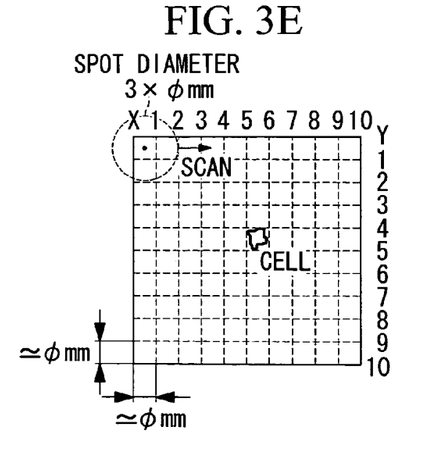
FIG. 3E is a view showing an example of an image of the cell examined and the spot of laser light irradiated, in the scanning laser microscope shown in FIG. 1.

FIGS. 3A to 3E show examples of an image of a cell observed and a spot of laser light irradiated according to the second embodiment of the present invention. FIGS. 3A and 3E are examples showing a state of the cell observed in the case where the zoom value Zoom is 1. In these figures, the cell is disposed at the pixel in the sixth position in the X direction and the fifth position in the Y direction. FIG. 3B shows an example of the case where the zoom value Zoom is 1 and the spot diameter of the irradiated laser light corresponds to a single pixel. FIG. 3C shows an example of the case where the zoom value. Zoom is 1 and the spot diameter of the irradiated laser light corresponds to three pixels. FIGS. 3B and 3C show the state where the laser scanning position is disposed at the pixel in the sixth position in the X direction and the fifth position in the Y direction in the field angle. FIG. 3D shows an example of an image showing a state of the cell observed in the case where the zoom value Zoom is 10, that is, an image in which the cell observed in FIG. 3A is observed at a zoom magnification ratio of ten.

For the sake of simplicity, the laser-scanning area for observation includes 10 pixels in the X direction and 10 pixels in the Y direction. However, the size of the laser-scanning area for observation is not limited thereto.

First, as shown in FIG. 3B, the case where the spot diameter of the irradiated laser light corresponds to a single pixel will be described.

Suppose that the system is configured as follows: As shown in FIG. 3A, when the zoom magnification ratio is one, the size of the cell approximately corresponds to the size of a single pixel, and as shown in FIG. 3B, the spot diameter $\phi$ [mm] of the irradiated laser light corresponds to the size of about a single pixel. In this case, if the total light intensity of the laser spot is P [mW], while the scanning is performed from the pixel disposed at the first position in the X direction and the first position in the Y direction to the pixel disposed at the tenth position in the X direction and the tenth position in the Y direction, the cell is irradiated with the laser light with the light intensity P [mW], which is the total light intensity of the laser spot, when the laser light is radiated onto the pixel disposed at the sixth position in the X direction and the fifth position in the Y direction.

When the above cell is observed at a zoom magnification ratio of ten, the cell is observed as shown in FIG. 3D. The size of the cell corresponds to the size of about 10×10=100 pixels. If the spot size of the laser beam is $\phi$ [mm] and the total light intensity is P [mm], which are the same as those in the above case, the sample 6 is scanned with a laser spot having a size about ten times the size of a single pixel, as shown in FIG. 3D. While the laser spot scans from the pixel disposed at the first position in the X direction and the first position in the Y direction to the pixel disposed at the tenth position in the X direction and the tenth position in the Y direction, the intensity of the laser light irradiated onto each pixel varies depending on the scanning position. When scanning is performed for one entire frame (i.e., from the pixel disposed at the first position in the X direction and the first position in the Y direction to the pixel disposed at the tenth position in the X direction and the tenth position in the Y direction), the intensity of the laser light irradiated onto each pixel is calculated according to the process shown in the flow chart in FIGS. 2A and 2B. In order to calculate the sum of the intensity of the laser light irradiated onto the cell by scanning one frame, all pixels included in the cell on the image (i.e., the part shown by the oblique lines in FIG. 3D) are selected and the intensities of light irradiated onto every selected pixel are added together.

Next, as shown in FIG. 3C, the case where the spot diameter of the irradiated laser light corresponds to three pixels will be described.

Suppose that the system is configured as follows: As shown in FIG. 3E, when the zoom magnification ratio is one, the size of the cell approximately corresponds to the size of a single pixel and the spot diameter of the irradiated laser light corresponds to the size of about three pixels (i.e., the laser spot diameter=3×$\phi$ [mm]). In this case, if the total light intensity of the laser spot is P [mW], while the scanning is performed from the pixel disposed at the first position in the X direction and the first position in the Y direction to the pixel disposed at the tenth position in the X direction and the tenth position in the Y direction, the cell is irradiated with the lower part of the laser spot when the laser light is radiated from the pixel disposed at the fifth position in the X direction and the fourth position in the Y direction to the pixel disposed at the seventh position in the X direction and the fourth position in the Y direction. In addition, the cell is irradiated with the central part of the laser spot when the laser light is radiated from the pixel disposed at the fifth position in the X direction and the fifth position in the Y direction to the pixel disposed at the seventh position in the X direction and the fifth position in the Y direction (in particular, the cell is irradiated with substantially the center of the laser spot at the pixel disposed at the sixth position in the X direction and the fifth position in the Y direction). In addition, the cell is irradiated with the upper part of the laser spot when the laser is radiated from the pixel disposed at the fifth position in the X direction and the sixth position in the Y direction to the pixel disposed at the seventh position in the X direction and the sixth position in the Y direction. The sum of these is equal to the intensity P' [mW] of light irradiated onto the cell. The intensity P' [mW] of light is calculated according to the process shown in the flow chart in FIGS. 2A and 2B.

Thus, with the laser light approximated to a Gaussian distribution, when the spot diameter of the laser light is increased compared with the size of a sample cell, the timing, the area, and the intensity of irradiation during scanning have a certain distribution, and thus it is difficult to determine the light intensity accurately. However, as in this embodiment, by calculating the power density per unit area and displaying the power density, the intensity of light irradiated onto an arbitrary-shaped sample to be observed can be determined and controlled at a predetermined time interval. Thereby, the observation can be performed while checking the degree of decoloring of the sample cell or estimating the time required for decoloring. Furthermore, regardless of the scanning conditions, such as the magnification ratio of the objective lens and the zoom magnification ratio, and the size of the cell that is observed, the irradiated power density can be determined per unit area.

A scanning laser microscope according to a third embodiment of the present invention will now be described with reference to FIGS. 4, 5, 6A, and 6B.

Figure 4:
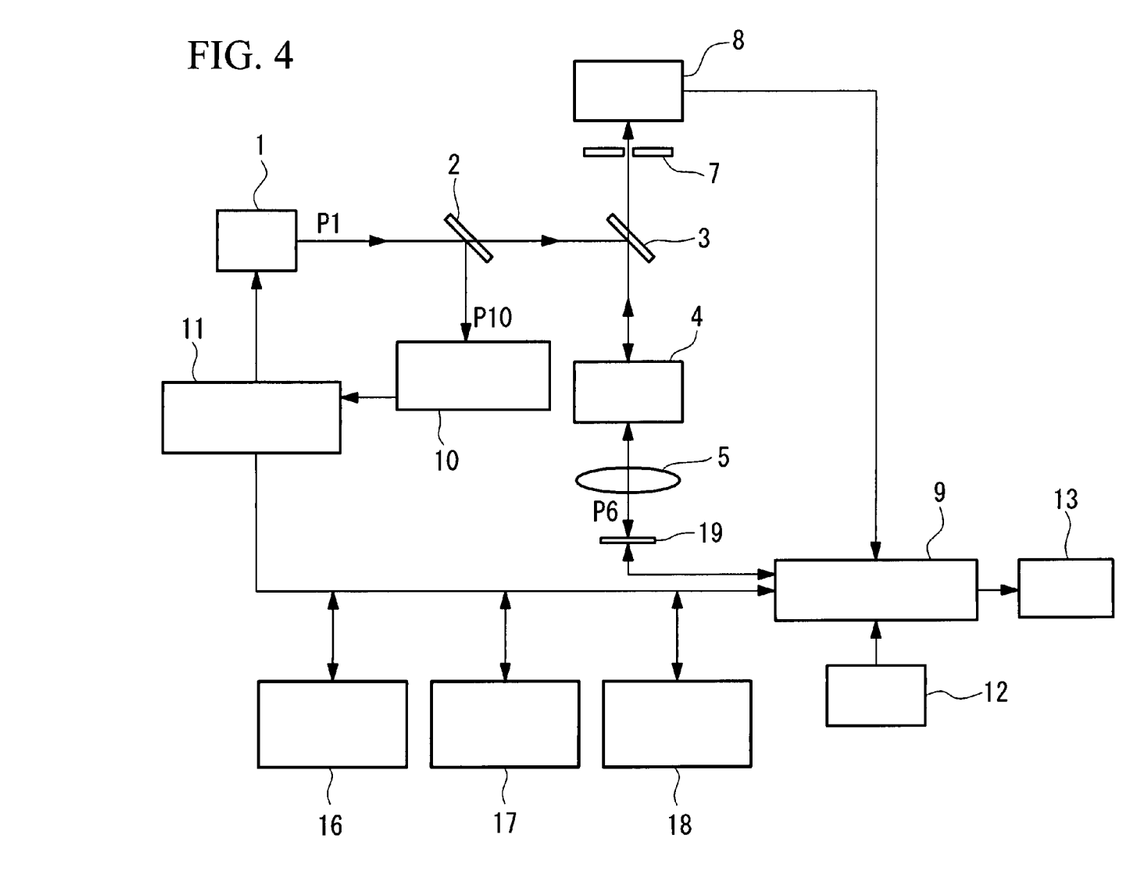
FIG. 4 is an overall structural diagram that schematically shows prescanning of a scanning laser microscope according to a third embodiment of the present invention.
Figure 5:
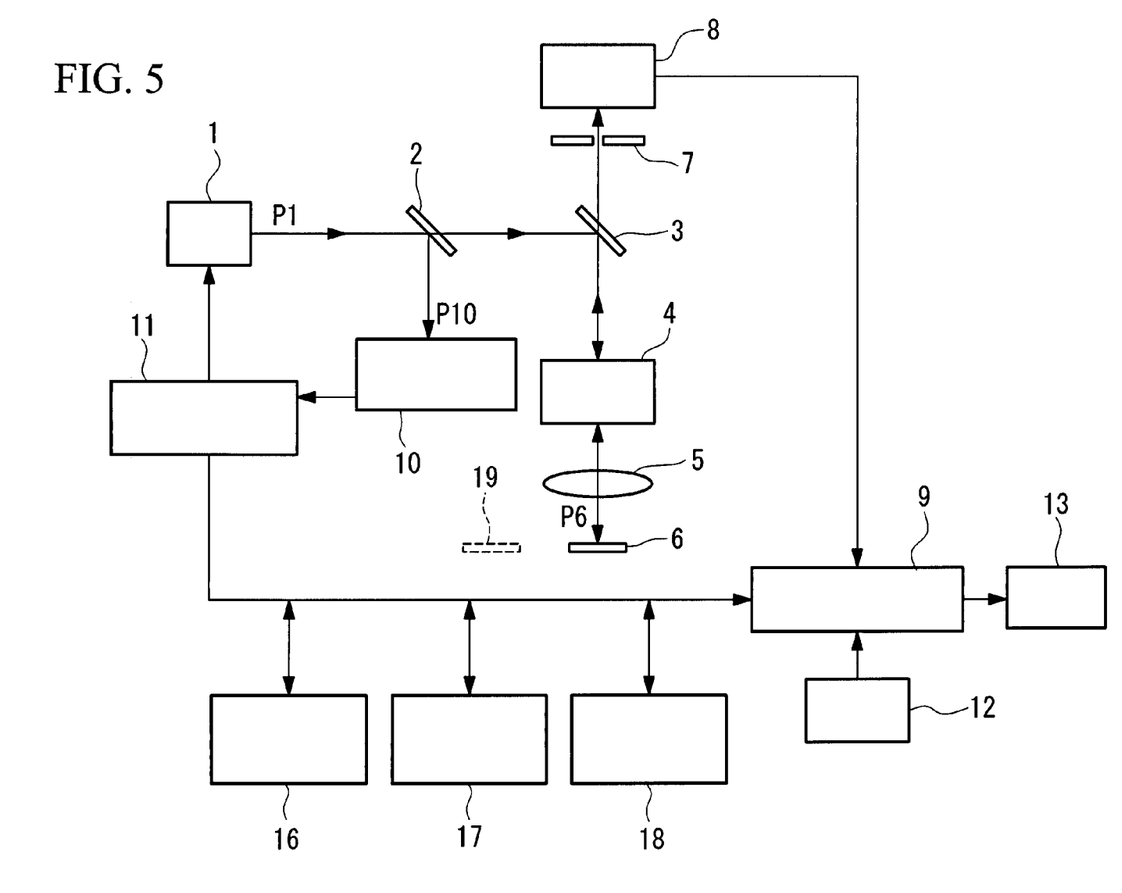
FIG. 5 is an overall structural diagram that schematically shows fluorescence observation of the scanning laser microscope shown in FIG. 4.

The scanning laser microscope of this embodiment performs a prescan for adjusting the light intensity prior to fluorescence observation. FIG. 4 shows the structure of the scanning laser microscope during the prescan for adjusting the light intensity before fluorescence observation. FIG. 5 shows the structure of the scanning laser microscope during fluorescence observation.

In this embodiment, parts common to the scanning laser microscope of the first and second embodiments shown in FIG. 1 are assigned the same reference numerals, and the description of those parts is omitted.

In FIGS. 4 and 5, a command-power sweep generating unit 16, a converted-power-density memory 17, and a command-power specifying unit 18 are connected to the system control unit 9. Each time one-frame scanning is completed, the command-power sweep generating unit 16 sweeps the power command value transmitted from the system control unit 9 to the laser light controller 11 so that the value is gradually changed from a small value to a large value or from a large value to a small value. The converted-power-density memory 17 is a memory that stores a converted power density at each pixel position (X, Y) on the sample 6, which is calculated by converting an observed value of the laser light intensity at the sample position detected by a light-intensity detector 19 described below. The command-power specifying unit 18 specifies a power command value which causes the power density of each pixel on the sample 6 to be a desired value, with reference to the converted-power-density memory 17.

When the prescan for adjusting the light intensity is performed, as shown in FIG. 4, the light-intensity detector 19 is disposed at the position of the sample 6 during fluorescence observation, and the intensity of the laser light emitted from the objective lens 5 is detected. The laser light intensity P 19 detected by the light-intensity detector 19 is sent to the system control unit 9. When the prescan for adjusting the light intensity is not performed, the light-intensity detector 19 is removed from the position of the sample 6 during fluorescence observation so as to provide a space on which the sample 6 can be placed.

When fluorescence observation is performed using the scanning laser microscope according to the third embodiment of the present invention having the above structure, first, as shown in FIG. 4, before the fluorescence observation is started, the sample 6 is removed and the light-intensity detector 19 is disposed at a position where the sample 6 is disposed. Subsequently, the power command value Pcmd of the laser light from the light source 1 and the area on the sample which the laser light irradiates are set by the operating unit 12, and the prescan for adjusting the light intensity is executed.

When executing the prescan for adjusting the light intensity, first, the command-power sweep generating unit 16 sets the minimum value in the range of power command values to be swept and instructs the minimum value to the laser light controller 11. The light source 1 emits laser light with a power corresponding to the instructed minimum power command value. The laser light controller 11 controls the light source 1 so that the intensity of light output from the light source 1 is made to follow the power command value on the basis of a reference light signal detected by the reference light detector 10.

In this state, the scanning unit 4 performs scanning.

The laser light intensity P19 at the sample position detected by the light-intensity detector 19 is sent to the system control unit 9. The system control unit 9 calculates the power density PDc(X, Y) at each pixel coordinate, as in the second embodiment, on the basis of the flowchart shown in FIGS. 6A and 6B, and displays the power density on the display unit 13. However, in FIGS. 6A and 6B, the output value P19 from the light-intensity detector 19 is used as the irradiation power at the sample without further processing, as shown in steps c1 and c2.

Figure 6A:
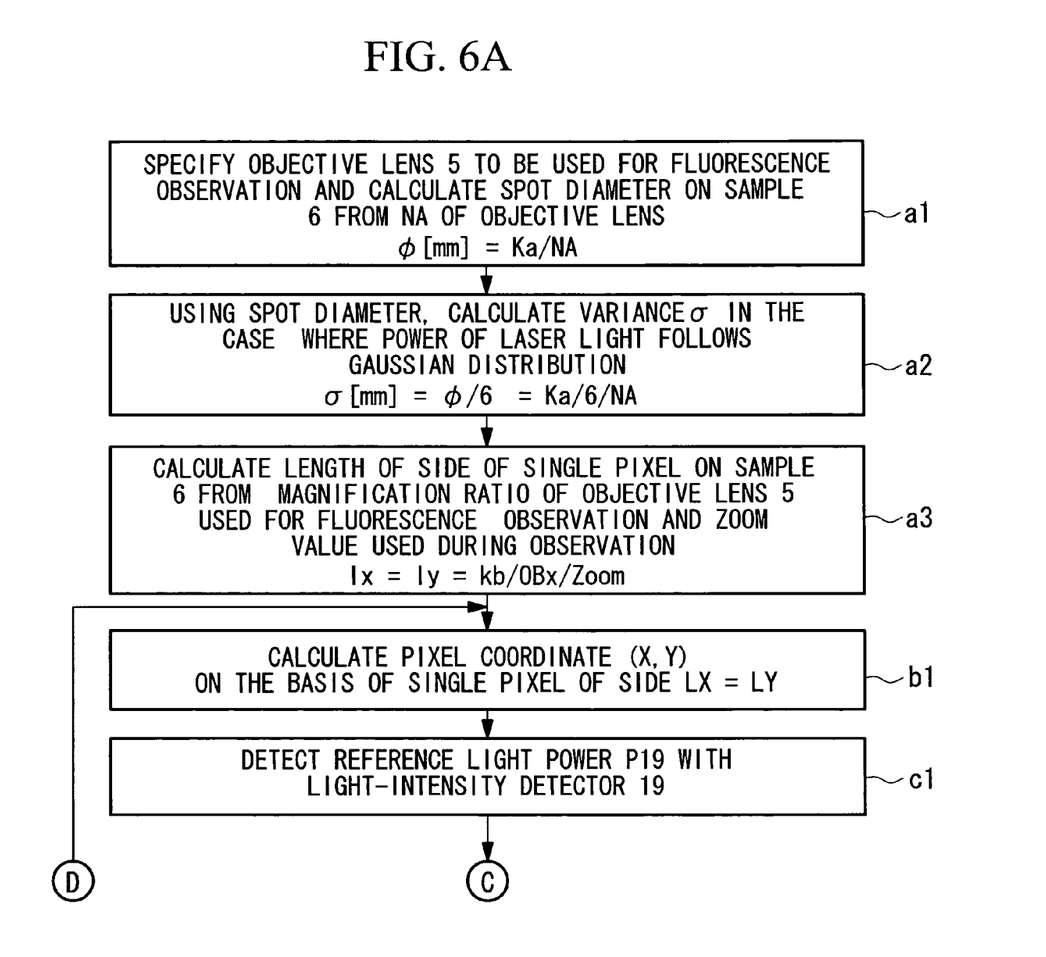
FIG. 6A is a flow chart showing an operation during prescanning for measuring a laser irradiation power of a sample in a system control unit of the scanning laser microscope shown in FIG. 4.

The calculated power density PDc(X, Y) in each pixel is transmitted to the converted-power-density memory 17 and is stored therein (step c3).

Figure 6B:
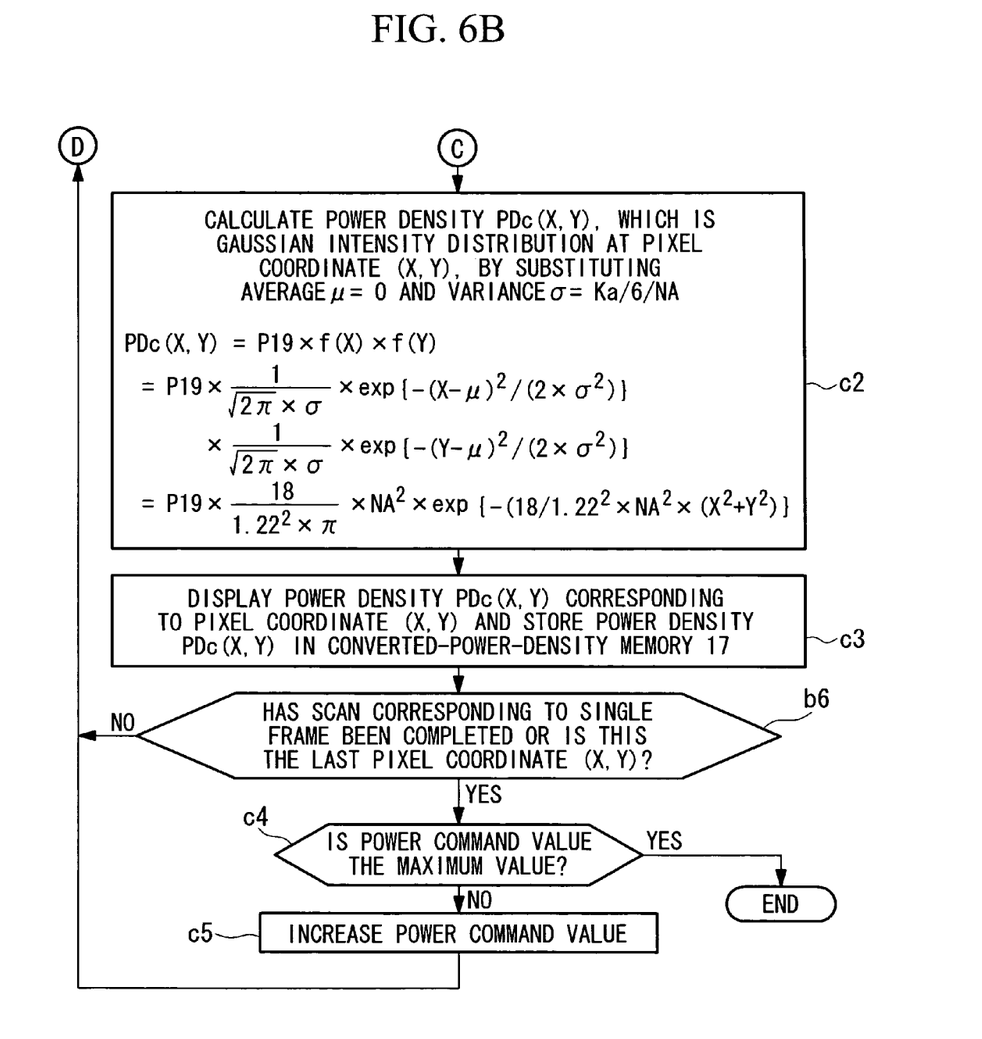
FIG. 6B is a flow chart showing an operation during prescanning for measuring a laser irradiation power of a sample in a system control unit of the scanning laser microscope shown in FIG. 4.

When a scan corresponding to one frame is completed, the command-power sweep generating unit 16 sets the power command value to a value slightly larger than the previous power command value and the same operation is repeated (steps c4 and c5). The series of operations is repeated until the swept power command value is set to the maximum value in the range. Eventually, the converted power density PDc(Pcmd, X, Y) is stored in the converted-power-density memory 17 in association with the power command value and the pixel coordinate.

When the maximum value in the range of power command values is set and a scan corresponding to one frame is then completed, the light-intensity detector 19 is removed and the sample 6 is disposed at the position at which the light-intensity detector 19 was disposed (the state shown in FIG. 5). Thus, the prescan for adjusting the light intensity is completed.

Normal fluorescence observation is then started. The fluorescence observation is performed while the power command is displayed and corrected with the reference light and while the power density in each pixel is displayed. In the display processing of the irradiation power and the power density in each pixel, the output P10 of the reference light detector 10, the observed value P19 of the irradiation power at the sample 6 corresponding to the power command value Pcmd, or the power density PDc(X, Y) in each pixel is read and displayed with reference to the converted-power-density memory 17. Accordingly, in this embodiment, the intensity of laser light irradiation during observation of the sample can be displayed on the basis of the observed value of the irradiation power at the sample 6.

The sample 6 may include a slide glass or a cover glass in addition to a cell. An oil-immersion objective lens or a water-immersion objective lens is used as the objective lens 5 in some cases. In such a case, a value, such as refractive index, associated with the substance disposed between the cell and the objective lens 5 may be input in advance, the intensity detected with the light-intensity detector 19 may be corrected, and the corrected intensity may be stored in the converted-power-density memory 17. This correction can also be performed during calculation of the intensity of irradiation light in the first embodiment and the second embodiment.

As described above, by performing the prescan for adjusting the light intensity prior to fluorescence observation, laser light can be emitted with a desired irradiation power onto the sample 6. In addition, since the reference light is also detected during fluorescence observation, the sample 6 can be stably irradiated with the laser light.

By referring to the value stored in the converted-power-density memory 17, the command-power specifying unit 18 specifies the optimum output of the laser light controller 11 with which the power command value Pcmd of the laser light set by the operating unit 12 is realized on the sample 6. The laser output may be controlled using this specified output of the laser light controller 11.

By extracting pixel coordinates (X, Y) included in the irradiation area of the laser light set by the operating unit 12 and calculating the sum of the power density values PDc(X, Y) of every pixel, the sum of the irradiation power on the specified area can be obtained. A power command value that is optimum for realizing the sum of the power density maybe specified and the laser output may be controlled on the basis of this power command value.

Furthermore, the powers and the power densities at all pixel coordinates (X, Y) can be instantaneously determined using a two-dimensional array element such as a charge coupled device (CCD) as the light-intensity detector 19.

In addition, the converted power density in each pixel on the sample 6 is calculated. Therefore, the laser light can be emitted with a desired irradiation power, even when the area on which the laser light is radiated is specified. Furthermore, the value converted to the power on the sample 6 is not calculated on the basis of the detected value from the reference light detector 10 and transmittance characteristic data of the optical system disposed between the reference light detector 10 and the sample 6, but is directly detected with the light-intensity detector 19 while the reference-light beamsplitting mirror 2, the dichroic mirror 3, the scanning unit 4, and the objective lens 5 are disposed in the actual system. Accordingly, in this scanning laser microscope, regardless of the individual differences between systems, the light intensity on the sample 6 can be determined more accurately.

Furthermore, during fluorescence observation, the display of the power or the power density can be updated or recorded each time the frame is renewed.

The structures of the functional blocks described with reference to the drawings in each embodiment do not necessarily correspond to the actual hardware structures. For example, a plurality of functional blocks can be realized as an integrated single hardware structure.

The laser light controller 11 in each embodiment has a function of controlling, for the light source 1, the wavelength and the intensity of the laser light to be emitted and a function of calculating the irradiation power on the sample on the basis of the reference light signal from the reference light detector 10. Among these, the function of calculating the irradiation power may be composed of hardware separated from the laser light controller 11 or may be realized by software in the system control unit 9.

In the display unit 13, it is also acceptable to display the irradiation power density without displaying the irradiation power. Furthermore, not only the time-integrated value of the power density but also the integrated value of the irradiation power of the entire beam may be calculated and displayed. By calculating the integrated value in each single frame, for example, as in the second embodiment, the total intensity of laser light irradiated for obtaining a single fluorescence image can be determined.

As described above, according to the present invention, since the value detected by the reference light detector (laser power monitor) is converted into the irradiation power of the laser light emitted from the objective lens in consideration of the characteristics of the intermediate optical system and is then displayed, the intensity of laser light irradiated onto the sample can be quantitatively determined.

Furthermore, the irradiation power per pixel can be determined when the observation is performed with a zoom function or the like.

What is claimed is:

1. A scanning laser microscope comprising:
    a light source configured to emit laser light;
    a scanning unit configured to scan the laser light emitted from the light source on a sample;
    a photodetector configured to detect light from the sample;
    a processing unit configured to convert a signal from the photodetector into an image signal of the sample;
    a reference light detector configured to detect part of the laser light emitted from the light source as a reference light signal;
    a laser light control unit configured to control the power of the laser light emitted from the light source;
    an irradiation-power calculation unit configured to calculate an irradiation power value at the sample on the basis of the reference light signal detected by the reference light detector; and
    a display unit configured to display the calculated irradiation power value at the sample.

2. The scanning laser microscope according to claim 1, wherein the irradiation-power calculation unit converts the reference light signal into the irradiation power value at the sample on the basis of transmittance characteristic data of an optical system disposed between the sample and the reference light detector.

3. The scanning laser microscope according to claim 1,
    wherein the irradiation-power calculation unit converts the reference light signal into the irradiation power value at the sample on the basis of transmittance characteristic data of an optical system disposed between the sample and the reference light detector, and
    the laser light control unit corrects the power of the laser light emitted from the light source on the basis of the irradiation power value.

4. The scanning laser microscope according to claim 1, wherein the irradiation-power calculation unit converts the reference light signal into the irradiation power value at the sample on the basis of at least one of spectral sensitivity characteristic data of the reference light detector and spectral transmittance characteristic data of an optical system disposed between the sample and the reference light detector.

5. The scanning laser microscope according to claim 1, wherein the irradiation-power calculation unit converts the reference light signal into an irradiation power value per unit area on the sample and the display unit displays the irradiation power value per unit area.

6. The scanning laser microscope according to claim 5, wherein the unit area corresponds to the size of a single pixel in a scan image of the sample.

7. The scanning laser microscope according to claim 1, further comprising:
    an irradiation-light-intensity detector disposed at the position of the sample; and
    a data storage unit configured to associate a power command value of the laser light control unit or the reference light signal from the reference light detector with a measured irradiation power value at the sample measured by the irradiation-light-intensity detector and to store the data,
    wherein the irradiation-power calculation unit determines an irradiation power by reading from the data storage unit the measured irradiation power value at the sample that is associated with the power command value or the reference light signal.

8. The scanning laser microscope according to claim 7, further comprising:
    a power-command specifying unit,
    wherein the irradiation-power calculation unit converts the irradiation power value at the sample into an irradiation power value per unit area on the sample,
    the power-command specifying unit specifies a power command value that can achieve a desired irradiation power value for a specific area on the sample on the basis of the irradiation power value per unit area, and
    the laser light control unit controls the light source on the basis of the power command value specified by the power-command specifying unit.

9. The scanning laser microscope according to claim 7, wherein the data storage unit stores the information on the irradiation power value per unit area converted from the irradiation power value at the sample.

10. The scanning laser microscope according to claim 5, wherein the irradiation-power calculation unit converts the reference light signal into the irradiation power value per unit area on the sample on the basis of a Gaussian density distribution.

11. The scanning laser microscope according to claim 5, wherein the display unit displays the irradiation power value per unit area, while updating the display after each pixel is scanned.

12. The scanning laser microscope according to claim 5, wherein the irradiation-power calculation unit calculates a time-integrated value of the irradiation power per unit area on the basis of the irradiation power value per unit area, and the display unit displays the time-integrated value of the irradiation power.

13. The scanning laser microscope according to claim 1, wherein the display unit displays the irradiation power value at the sample, while updating the display after each pixel is scanned.

14. The scanning laser microscope according to claim 12, wherein the irradiation-power calculation unit integrates the irradiation power per unit area while laser scanning is performed once.

15. The scanning laser microscope according to claim 1, wherein the irradiation-power calculation unit calculates a time-integrated value of the irradiation power on the sample and the display unit displays the time-integrated value.

16. The scanning laser microscope according to claim 15, wherein the irradiation-power calculation unit integrates the irradiation power value at the sample while laser scanning is performed once.

17. A scanning laser microscope comprising:
a light source configured to emit laser light;
a scanning unit configured to scan the laser light emitted from the light source on a sample;
a photodetector configured to detect light from the sample;
a processing unit configured to convert a signal from the photodetector into an image signal of the sample;
a reference light detector configured to detect part of the laser light emitted from the light source as a reference light signal;
a control device configured to control the power of the laser light emitted from the light source;
an irradiation-power calculation device configured to calculate an irradiation power value at the sample on the basis of the reference light signal detected by the reference light detector; and
a display unit configured to display the calculated irradiation power value at the sample.

18. The scanning laser microscope according to claim 17, wherein the irradiation-power calculation device calculates an irradiation power value per unit area on the sample on the basis of the reference light signal, and the display unit displays the irradiation power value per unit area.

19. The scanning laser microscope according to claim 17, further comprising:
a data storage device configured to associate a measured irradiation power value at the sample with a power command value from the control device to the light source or the reference light signal and to store the data,
wherein the irradiation-power calculation device determines an irradiation power value by reading from the data storage device the measured irradiation power value that is associated with the power command value or the reference light signal.

20. A scanning laser microscope comprising:
a light source configured to emit laser light;
a scanning unit configured to scan the laser light emitted from the light source on a sample;
a photodetector configured to detect light from the sample;
a processing unit configured to convert a signal from the photodetector into an image signal of the sample;
a reference light detector configured to detect part of the laser light emitted from the light source as a reference light signal;
a laser light control unit configured to control the power of the laser light emitted from the light source;
an irradiation-power calculation unit configured to calculate an irradiation power value per unit area on the sample on the basis of the reference light signal detected by the reference light detector; and
a display unit configured to display the calculated irradiation power value per unit area on the sample.

* * * * *